(12) United States Patent
Chu

(10) Patent No.: US 10,777,063 B1
(45) Date of Patent: Sep. 15, 2020

(54) SYSTEMS AND METHODS FOR IDENTIFYING VAPING

(71) Applicant: Soter Technologies, LLC, Ronkonkoma, NY (US)

(72) Inventor: Cary Chu, Mount Sinai, NY (US)

(73) Assignee: SOTER TECHNOLOGIES, LLC, Ronkonkoma, NY (US)

( * ) Notice: Subject to any disclaimer, the term of this patent is extended or adjusted under 35 U.S.C. 154(b) by 0 days.

(21) Appl. No.: 16/812,969

(22) Filed: Mar. 9, 2020

(51) Int. Cl.
| | |
|---|---|
| *G08B 17/10* | (2006.01) |
| *G08B 21/12* | (2006.01) |
| *H04L 12/10* | (2006.01) |
| *G01N 1/22* | (2006.01) |
| *G08B 1/08* | (2006.01) |

(52) U.S. Cl.
CPC ........... *G08B 21/12* (2013.01); *G01N 1/2273* (2013.01); *G08B 1/08* (2013.01); *G08B 17/10* (2013.01); *H04L 12/10* (2013.01)

(58) Field of Classification Search
CPC .......... G08B 21/12; G08B 1/08; G08B 17/10; G01N 1/2273; H04L 12/10
See application file for complete search history.

(56) References Cited

U.S. PATENT DOCUMENTS

| | | | | |
|---|---|---|---|---|
| 3,933,029 A | * | 1/1976 | Rabenecker | G01N 1/24 73/31.05 |
| 5,261,596 A | * | 11/1993 | Tachibana | F24F 11/30 236/49.3 |
| 5,451,929 A | * | 9/1995 | Adelman | F24F 3/1603 165/11.1 |
| 5,856,780 A | * | 1/1999 | McGeehin | G01N 33/0063 340/540 |
| 6,711,470 B1 | * | 3/2004 | Hartenstein | F24F 11/30 700/276 |
| 6,998,991 B1 | * | 2/2006 | Goldstein | G01N 21/783 340/628 |

(Continued)

FOREIGN PATENT DOCUMENTS

| | | |
|---|---|---|
| CA | 2740454 C | 11/2015 |
| KR | 101778681 B1 | 9/2017 |

(Continued)

OTHER PUBLICATIONS

International Preliminary Report on Patentability dated Feb. 18, 2020 by the U.S. Patent and Trademark Office, acting as International Searching Authority in corresponding International Application No. PCT/US2018/000223.

(Continued)

*Primary Examiner* — Quang Pham
(74) *Attorney, Agent, or Firm* — Carter, DeLuca & Farrell LLP; George Likourezos

(57) ABSTRACT

Systems and sensors for detecting vaping or smoking are disclosed. A sensor system for identifying vaping and smoking at a site includes an air sensor located within a return vent of a ventilation system and configured to sense air quality of air conveyed through the return vent, a controller configured to identify vaping and smoking from the sensed air quality based on an air signature, and a network interface configured to communicate an alert indicating the vaping or smoking, when the vaping or smoking is identified.

23 Claims, 6 Drawing Sheets

(56) References Cited

U.S. PATENT DOCUMENTS

| | | | | |
|---|---|---|---|---|
| 8,175,297 | B1* | 5/2012 | Ho | H04R 1/26 381/122 |
| 2002/0152792 | A1* | 10/2002 | Wang | A61L 2/208 73/1.02 |
| 2005/0199735 | A1* | 9/2005 | Eisenhour | G01K 7/42 236/1 C |
| 2008/0300817 | A1* | 12/2008 | Bieswanger | G06F 11/30 702/116 |
| 2010/0127865 | A1* | 5/2010 | Marriam | G08B 1/08 340/541 |
| 2013/0255482 | A1* | 10/2013 | Goodson | F23J 15/022 95/3 |
| 2013/0284192 | A1* | 10/2013 | Peleg | A24F 47/004 131/329 |
| 2014/0202787 | A1* | 7/2014 | Richardson | H04B 1/3888 181/202 |
| 2014/0260692 | A1* | 9/2014 | Sharp | G01N 1/2273 73/863.23 |
| 2015/0020614 | A1* | 1/2015 | Gettings | G01F 1/00 73/865.8 |
| 2015/0153171 | A1* | 6/2015 | Zhou | G01C 5/06 702/138 |
| 2015/0235652 | A1* | 8/2015 | Moser | G10K 11/002 379/392.01 |
| 2015/0241993 | A1* | 8/2015 | Gallo | H04L 67/18 345/156 |
| 2015/0256355 | A1* | 9/2015 | Pera | H04L 12/2823 700/90 |
| 2015/0323427 | A1* | 11/2015 | Sharp | G01N 1/2273 73/863.23 |
| 2016/0050037 | A1* | 2/2016 | Webb | G08B 27/005 455/3.01 |
| 2016/0063841 | A1* | 3/2016 | Schultz | G06F 13/4221 340/601 |
| 2016/0102879 | A1* | 4/2016 | Guest | G05B 15/02 700/276 |
| 2016/0163168 | A1* | 6/2016 | Brav | G08B 21/043 381/56 |
| 2016/0212828 | A1* | 7/2016 | Leinen | H05B 47/18 |
| 2016/0260513 | A1* | 9/2016 | Pan | G01N 15/1056 |
| 2017/0023457 | A1* | 1/2017 | Hart | G01N 15/1459 |
| 2017/0042247 | A1* | 2/2017 | Xiang | H05B 1/0244 |
| 2017/0055572 | A1* | 3/2017 | Utley | G16H 40/67 |
| 2017/0227508 | A1* | 8/2017 | Cai | A61B 5/097 |
| 2017/0284690 | A1* | 10/2017 | Lipanov | F24F 11/0001 |
| 2017/0309091 | A1* | 10/2017 | Cameron | G07C 5/0825 |
| 2017/0321923 | A1* | 11/2017 | Wiens-Kind | G05B 19/042 |
| 2018/0050230 | A1* | 2/2018 | Toland | H04M 1/72527 |
| 2018/0286208 | A1* | 10/2018 | Baker | H04W 4/023 |
| 2019/0108739 | A1* | 4/2019 | Wedig | G08B 29/188 |
| 2020/0011779 | A1* | 1/2020 | Lavrovsky | G01N 15/0205 |

FOREIGN PATENT DOCUMENTS

| | | | | |
|---|---|---|---|---|
| WO | 2019035950 | A1 | | 2/2019 |
| WO | WO-2019035950 | A1 | * | 2/2019 ............ G08B 21/12 |
| WO | 2020005431 | A1 | | 1/2020 |

OTHER PUBLICATIONS

International Search Report and Written Opinon issued by the U.S. Patent and Trademark Office acting as International Searching Authority in corresponding International Application No. PCT/US18/00223 dated Nov. 15, 2018.

The MagPi Magazine, "Raspberry PI 3: Specs, Benchmarks & Testing," Dec. 31, 2016, retrieved on Apr. 19, 2019 from https://www.raspberrypi.org/magpi/raspberry-pi-3-specs-benchmarks/.

International Search Report and Written Opinion issued by the U.S. Patent and Trademark Office acting as International Searching Authority in International Application No. PCT/US2019/018532 dated May 1, 2019.

Office Action issued by the U.S. Patent and Trademark Office dated Jul. 17, 2020 in corresponding U.S. Appl. No. 16/824,347.

* cited by examiner

_(12) United States Patent_  _(10) Patent No.: US 10,777,063 B1_

SYSTEMS AND METHODS FOR IDENTIFYING VAPING

BACKGROUND

Technical Field

The present disclosure relates to systems and methods for identifying vaping at an enclosed site. More particularly, the present disclosure relates to a system which is installed in a ventilation system and includes an air quality sensor for detecting vaping.

Background of Related Art

Vaping has become a serious concern in enclosed areas due to hazardous/harmful effects on people. Such concerns can occur in various settings, including classrooms, restrooms, bathrooms, storage rooms, hospital rooms, or other kinds of enclosed areas in a school, hospital, warehouse, cafeteria, offices, financial institutes, governmental buildings, or any business entities. In certain settings, vaping/smoking can be identified by camera surveillance. However, such camera surveillance systems are not permitted or are not appropriate in private areas such as restrooms, bathrooms, shower rooms, or hospital rooms because privacy concerns have higher priority. Accordingly, there is interest in improving and developing vape detection technologies for various settings.

SUMMARY

The present disclosure relates to systems which are installed in a ventilation system and include an air quality sensor for identifying vaping.

In aspects of the present disclosure, a sensor system for identifying vaping and smoking at a site includes an air sensor located within a return vent of a ventilation system and configured to sense air quality of air conveyed through the return vent, a controller configured to identify vaping and smoking from the sensed air quality based on an air signature, and a network interface configured to communicate an alert indicating the vaping or smoking, when the vaping or smoking is identified.

In various embodiments of the sensor system, the sensor system includes a power connection implementing at least one of: Power over Ethernet, Power over Ethernet+, or power by a power outlet.

In various embodiments of the sensor system, the air sensor is configured to sample the air conveyed through the return vent at a sampling rate based on airflow of the air conveyed through the return vent. In various embodiments of the sensor system, the sampling rate for a higher airflow is greater than the sampling rate for a lower airflow. The air sensor includes a sensitivity setting, which is configured to be more sensitive for a higher airflow than for a lower airflow.

In various embodiments of the sensor system, the air sensor is trained by data collected at the site during a predetermined period in a learning mode prior to identification of the vaping or smoking.

In various embodiments of the sensor system, the air sensor includes internal sensitivity parameters, and the controller is configured to adjust the internal sensitivity parameters based on the collected data during the predetermined period in the learning mode.

In various embodiments of the sensor system, the controller is configured to adjust the internal sensitivity parameters by comparing the collected data with the air signature.

In various embodiments of the sensor system, the air signature includes a temperature range, a hydrogen range, a humidity range, total volatile organic compound range, a particulate concentration range, and a particulate mass range.

In various embodiments of the sensor system, the alert includes at least one of a text message, an email, an optical flashing, or an audible sound.

In aspects of the present disclosure, a detection system for identifying vaping and smoking at a site includes a ventilation system including a return vent, and a sensor system located within the return vent. The sensor system includes an air sensor configured to sense air quality of air conveyed through the return vent, a controller configured to identify vaping and smoking from the sensed air quality based on an air signature, and a network interface configured to communicate an alert indicating the vaping or smoking, when the vaping or smoking is identified.

In various embodiments of the detection system, the sensor system includes a power connection implementing at least one of: Power over Ethernet, Power over Ethernet+, or power by a power outlet.

In various embodiments of the detection system, the air sensor is configured to sample the air conveyed through the return vent at a sampling rate based on airflow of the air conveyed through the return vent. In various embodiments of the detection system, the sampling rate for a higher airflow is greater than the sampling rate for a lower airflow. The air sensor includes a sensitivity setting, which is configured to be more sensitive for a higher airflow than for a lower airflow.

In various embodiments of the detection system, the air sensor is trained by data collected at the site during a predetermined period in a learning mode prior to identification of the vaping or smoking.

In various embodiments of the detection system, the air sensor includes internal sensitivity parameters, and the controller is configured to adjust the internal sensitivity parameters based on the collected data during the predetermined period in the learning mode.

In various embodiments of the detection system, the controller is configured to adjust the internal sensitivity parameters by comparing the collected data with the air signature.

In various embodiments of the detection system, the air signature includes a temperature range, a hydrogen range, a humidity range, a total volatile organic compound range, a particulate concentration range, and a particulate mass range.

In various embodiments of the detection system, the alert includes at least one of: a text message, an email, an optical flashing, or an audible sound.

In aspects of the present disclosure, a method for identifying vaping and smoking at a site includes collecting data at a site by an air sensor located within a return vent of a ventilation system during a predetermined period in a learning mode, adjusting based on the collected data internal sensitivity parameters of the air sensor for identifying the vaping or smoking, sensing air quality by the air sensor of air conveyed through the return vent, identifying vaping or smoking from the sensed air quality based on an air signature, and communicating an alert when the vaping or smoking is identified.

In various embodiments of the method, the air signature includes a temperature range, a hydrogen range, a humidity range, a total volatile organic compound range, a particulate concentration range, and a particulate mass range.

In various embodiments of the method, adjusting the internal sensitivity parameters includes adjusting the internal sensitivity parameters of the air sensor by comparing the collected data with the air signature.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A better understanding of the features and advantages of the disclosed technology will be obtained by reference to the following detailed description that sets forth illustrative embodiments, in which the principles of the technology are utilized, and the accompanying drawings of which.

DETAILED DESCRIPTION

This disclosure relates to detection systems and detection sensors for detecting air quality to identify whether vaping or smoking activities are occurring in enclosed sites. The detection systems and detection sensors are installed in a return vent of a ventilation system. When vaping is identified, warnings or alerts may be communicated to registered users or clients without providing any indication of warnings to one or more persons who vaped or are vaping at the site. In this way, one or more persons who vape can be timely intercepted. Aspects of vape detection are described in International Patent Application Publication No. WO2019035950A1, which is hereby incorporated by reference herein in its entirety.

Figure 1A:
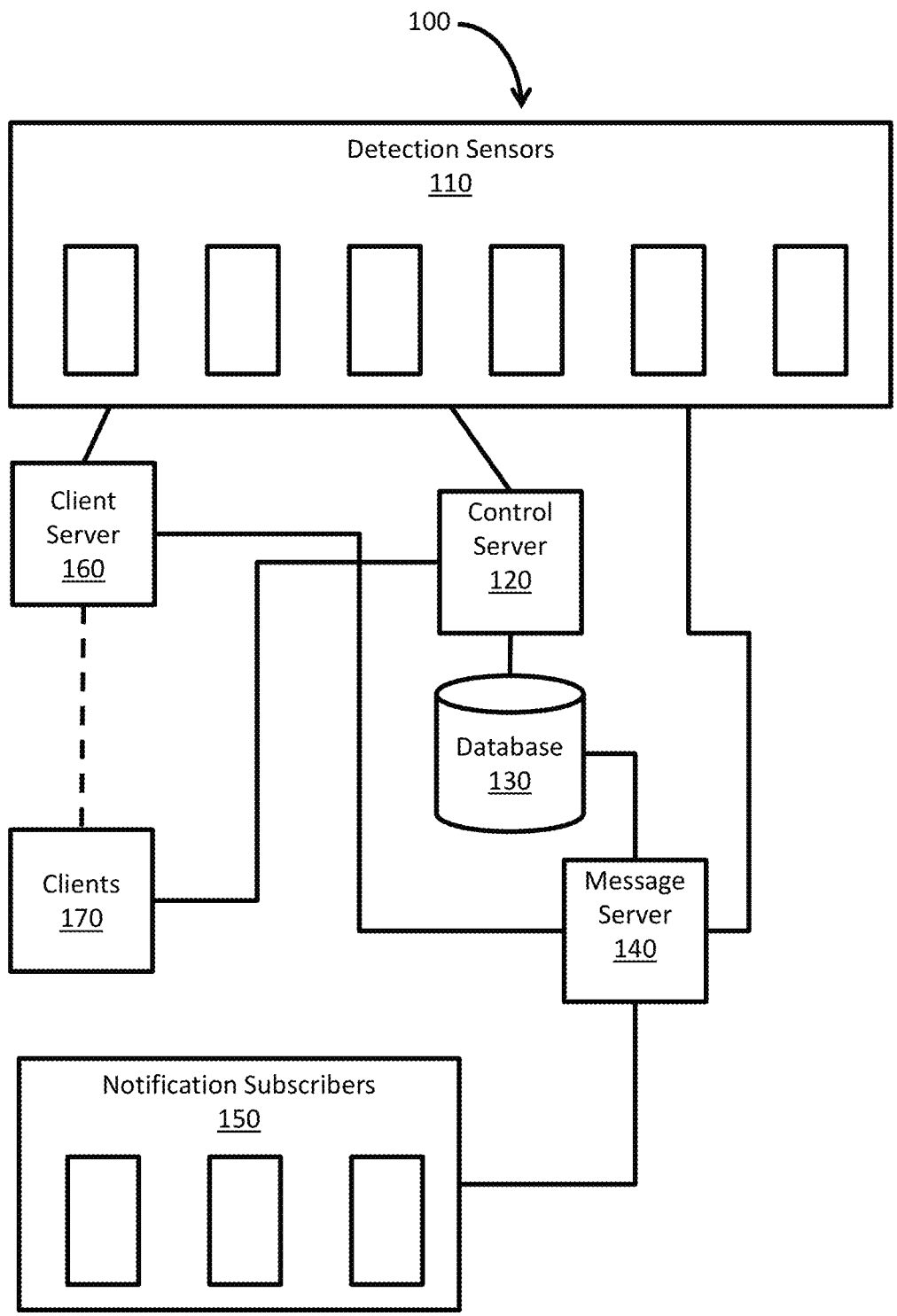
FIG. 1A is a block diagram of an exemplary detection system for identifying vaping/smoking in accordance with embodiments of the present disclosure.

FIG. 1A illustrates a block diagram showing a detection system 100 according to embodiments of the present disclosure. The detection system 100 may include a plurality of detection sensors 110, which detect air quality related to vaping. The detection system 100 may also include a sound sensor to detect sound related to noise disturbance at enclosed sites. The detection system 100 further includes a control server 120 for determining whether or not vaping occurs at the enclosed site, and a database 130 storing base data for identifying vaping and history data of detected sounds and air quality at each enclosed site.

In various embodiments, the detected air quality may be analyzed by the detection sensors 110 or the detected air quality may be communicated to the control server 120. In various embodiments, the control server 120 may analyze the detected air quality, and determine whether vaping activities occur at the enclosed sites based on base data. In an aspect, the base data may be location-independent, meaning that the base data is the same for every enclosed location at every time. The location-independent base data may be air quality data related to identifying vaping. In various embodiments, vaping may be identified based on signature, which includes a temperature range, a humidity range, a hydrogen range, a total volatile organic compound range, a particulate concentration range, and a particulate mass range. In an aspect, features for identifying vaping may be integrated into the detection sensor 110 so that the detection sensor 110 may request an alert or warning message to be sent to the clients 170, when the signature is identified in the detected air quality. In various embodiments, the signature may include combination of predetermined ranges of temperature, humidity, and hydrogen.

Generally, hydrogen sensors require at least 7 volts and about 1,000-ohm resistance. The detection sensor 110, however, may have a modified hydrogen sensor, which requires much lower voltage and a much higher resistance. The voltage and resistance may vary based on temperature of the environment. Other air sensors for sensing various air quality characteristics described herein will be understood by persons skilled in the art, and such air sensors can be incorporated into the detector sensor 110.

The database 130 may further include history data which is time-series and location-specific data for identifying vaping for each location where the detection sensor 110 has been installed. In an aspect, the control server 120 may analyze the history data to predict occurrences of vaping at the location so that appropriate or precautionary actions may be proactively taken at the location.

In an aspect, the control server 120 may analyze the history data stored at the database 130 to identify trend of the history data. The trend may be a decreasing or increasing pattern of occurrences of vaping. In case when a decreasing or increasing pattern is identified, the control server 120 may adjust the base data for identifying vaping to make the detection sensor 110 more or less sensitive to the identification. In this way, the base data may be adjusted based on the trend of the history data.

Figure 3:
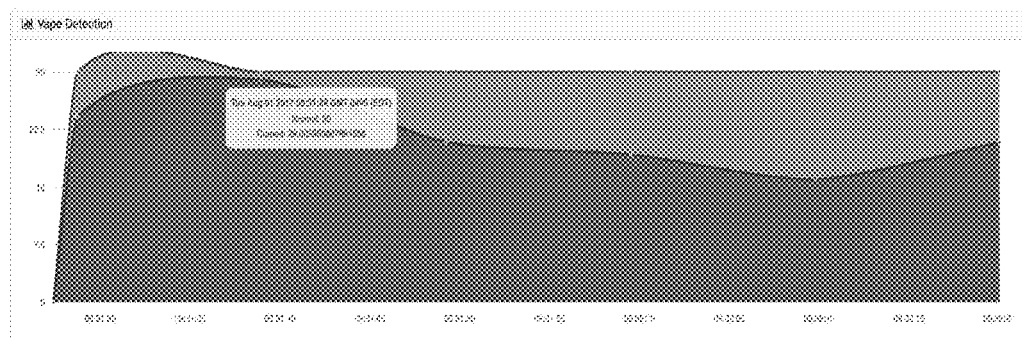
FIG. 3 is a graphical illustration showing exemplary data collected by a sensor in accordance with embodiments of the present disclosure.

For example, FIG. 3 shows history data of detected air quality. The horizontal axis for the history data represents time, and the vertical axis represents air quality index. The history data obtained during the learning mode is used to generate base data for identifying vaping at the installation location in the active mode. Internal sensitivity parameters of the detection sensor 110 may be updated/adjusted based on the base data. In an aspect, the internal sensitivity parameters may be updated/adjusted by comparing the base data with the signature.

In an aspect, the detection sensors 110 may repeat the learning mode and active mode consecutively. As shown in FIG. 3, the first period (e.g., about ten seconds from the start to 09:31:38) may be used in the learning mode to collect data regarding the environment. Then, the detection sensor 110 determines whether an adjustment or calibration needs to be made to the air sensors so as to properly detect vaping. For example, the voltage or resistance in the air sensors varies depending on temperature of the environment. Thus, the air sensors can be adjusted or calibrated based on the environment. In embodiments, the air sensor may be a hydrogen sensor.

After the first period for collecting environment-calibrated data, the threshold value for vaping is determined in the active mode for a second period and the detection sensor 110 detects vaping based on the threshold value.

FIG. 3 shows two curves. The upper curve represents threshold index value for identifying vaping. The lower curve represents the history data of detection results from the air quality sensor of the detection sensor 110 (FIG. 1). The upper curve is stabilized in a period of time after the power-up.

In an aspect, the detection sensors 110 may repeat the learning mode and active mode repeatedly. As shown in FIG. 3, the first period (e.g., about ten seconds from the start to 09:31:38) may be used in the learning mode to collect data regarding the environment. Then, the detection sensor 110 determines whether an adjustment or calibration needs to be made to the air sensors so as to properly detect vaping. For example, the voltage or resistance in the modified hydrogen sensor varies depending on temperature of the environment. Thus, the air sensors can be adjusted or calibrated based on the environment data.

After the first period for collecting environment-calibrated data, the threshold value for vaping is determined in the active mode for a second period and the detection sensor 110 detects vaping based on the threshold value.

The index value may be calculated based on the temperature, moisture, and the detection results of the air sensors. For example, the temperature falls in a range between 60- and 80-degree Fahrenheit, the moisture is increased by at least 10 percent, and the hydrogen increases from the base level (e.g., environment level) by approximately 10 percent, the detection sensor 110 may determine that vaping has occurred. This determination is provided as an example and is not provided to limit the scope of this application.

In an aspect, and referring again to FIG. 1, the control server 120 may send a command to the detection sensor 110 to adjust internal parameters for detecting vaping based on the trend identified from the history data. Further, the control server 120 may communicate with the detection sensors 110 by calling functions of application programming interface ("API") between the detection sensor 110 and the control server 120. In this regard, the detection sensor 110 can push detection results to the control server 120 and respond to the request by the control server 120.

In an aspect, the control server 120 may not store detected results from the detection sensors 110 because of privacy issues. Nevertheless, the control server 120 may provide signals back to the detection sensors 110 to indicate tuning parameters and false positives.

Internal parameters of the detection sensor 110 may include one or more of LED functionality, sound threshold, networking server IP address, alert timeout, serial number, reboot for device required or not, latest binary code, and/or vape identification algorithm parameters, among other things. This list of parameters is exemplary and is not exhaustive. Parameters for identifying vaping may include a window size or threshold values or ranges for identifying vaping.

In an aspect, the control server 120 may update the internal parameters via text or binary files. Each of the internal parameters of the detection sensor 110 may be saved in the database 130.

In another aspect, the control server 120 may control the detection sensors 110 collectively, individually, or group by group. For example, several detection sensors 110 may be installed at the same site. When they need to update internal parameters or settings, the control server 120 may control the detection sensors 110 collectively at the site. However, such control may not affect the detection sensor 110 installed in the other sites. The control server 120 may use a query language to request data from the database 130. The query language may be SQL, MySQL, SSP, C, C++, C #, PHP, SAP, Sybase, Java, JavaScript, or any language, which can be used to request data from a database.

In yet another aspect, even when several detection sensors 110 are installed at the same site, the control server 120 may control them differently because one detection sensor 110 may have different parameters for identifying vaping from those of another detection sensor 110 due to different installation locations at the site. For example, the detection sensor 110 installed at a bedroom has parameters different from those of the detection sensor 110 installed at a bathroom.

Clients 170 may log in to the control server 120 to see graphical representations of the detection results from the detection sensor 110 via Internet. Communication between the clients 170 and the control server 120 may utilize http, https, ftp, SMTP, or related Internet protocols. The clients 170 may be able to adjust settings for each the detection sensor 110. For example, the settings may include a mode of warnings (e.g., an email, text message, telephone call, instant message, audible warning, etc.), an address, to which such warnings are to be sent in case of identification of vaping, and the like. The clients 170 are the ones who are responsible for the sites where the detection sensors 110 are installed for identifying vaping. For example, the clients 170 may be a principal, vice president, or person in charge at a school, a president at a company, a manager at a hospital or any commercial establishment, or security personnel. This list, however, is not meant to be exhaustive but is provided only for showing examples. Other people having different positions at different locations can be included in this list.

When the detection sensor 110 identifies vaping, the detection sensor 110 may send an alert to the clients 170 via a client server 160 using Internet protocols. The client server 160 may be used for sending a simple message or email to the clients 170 responsible for the site where the vaping is detected. The client server 160 may manage the clients 170 registered on the client server 160 and show alert history and other notification upon requests from the clients 170. Further, the client server 160 may handle customizing or fine tuning the detection sensors 110. Such customization may provide an alert indicating the detection sensors 110 need to be rebooted, updated, or receive configuration.

In an aspect, as dotted lines shown in FIG. 1, the communication between the client server 160 and the clients 170 may not be regularly performed but can be performed only when vaping is identified. The clients 170 may receive the alert on a computer, smart device, or mobile phone. In this way, the clients 170 are not inundated by overwhelming numbers of messages because they receive the alert only when vaping is identified. Further, the clients 170 may be able to timely and properly supervise at the site whenever an alert is received.

When the client server 160 receives an alert from the detection sensor 110, the client server 160 may communicate with the message server 140, which manages pushing alerts to the notification subscribers 150. In various embodiments, the clients 170 may be the persons in charge as the first contact person who has a direct access to the control server 120 for the site, and the notification subscribers 150 may be any related personnel as second contact persons who do not have a direct access to the control server 120. Similar to the ways the client server 160 sends alerts to the clients 170, the message server 140 sends alerts to the notification subscribers 150 via a text message, email, instant message, telephone call, audible warning, or any communication means readily available to a person having skill in the art. The notification subscribers 150 may receive alerts via a computer, smart device, mobile phone, personal digital assistant, tablet, or any available means for receiving such alerts.

As described above, vaping can be identified when the signature is detected, such that vaping can be identified independent of locations and times. Thus, features related to identification of vaping may be integrated into the detection sensor 110. In this case, when vaping is identified, the detection sensor 110 may bypass the control server 120 and directly communicate with the message server 140 and the client server 160 to transmit alerts to persons in charge or responsible for the sites where the detection sensor 110 are installed.

Figure 1B:
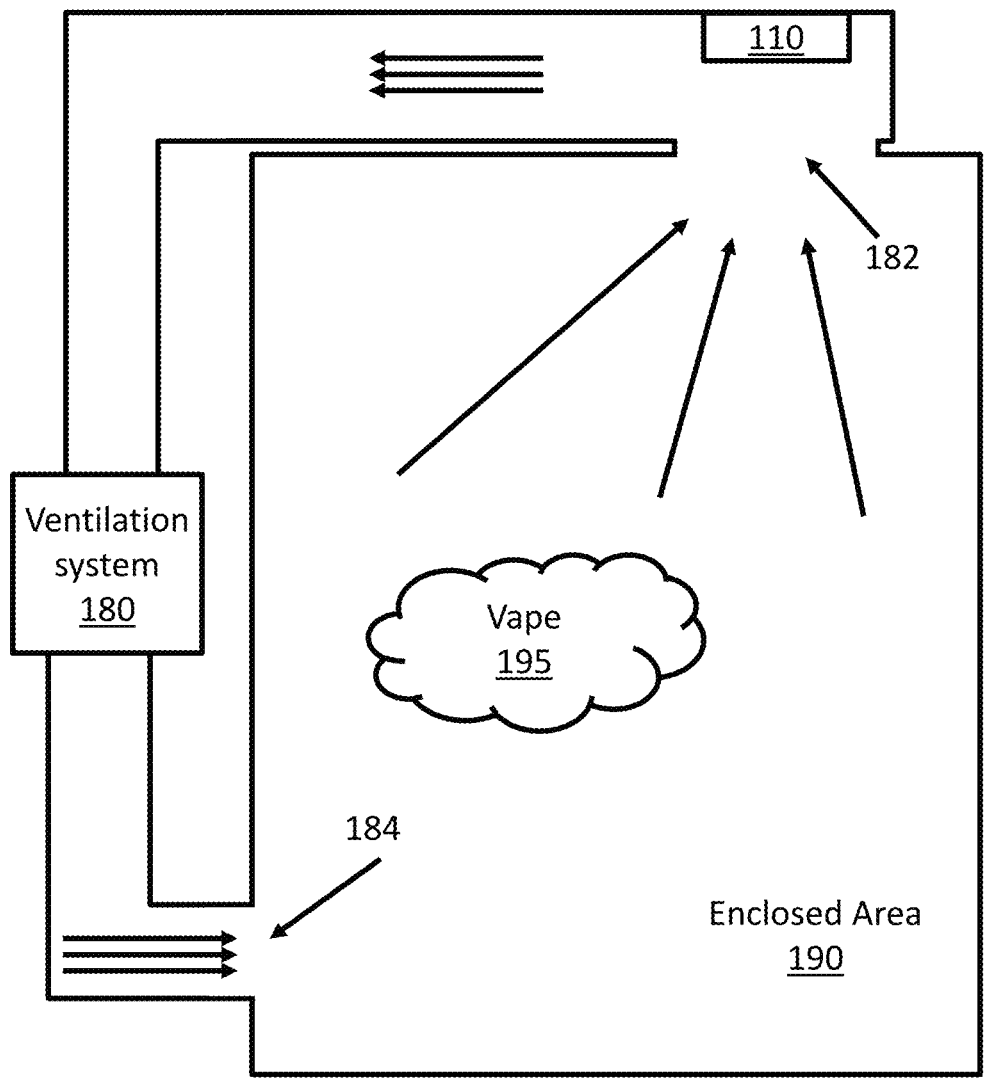
FIG. 1B is a diagram of the detection system of FIG. 1A installed in a ventilation system in accordance with embodiments of the present disclosure.

Even when vaping generates a cloud of gas at an enclosed site, the detection sensor 110 might not be able to identify the vaping in a case when the cloud of gas from the vaping does not move to the detection sensor 110. In this regard, the air needs to move to the detection sensor 110. In accordance with aspects of the present disclosure, the detection sensor 110 may be installed in a return vent of a ventilation system 180, as shown in FIG. 1B. The ventilation system 180 may force or facilitate circulation of air in an enclosed area 190, such as a bathroom, bedroom, shower room, office, lecture room, hotel room, classroom, storage, restaurant, and/or business establishment, among others. The ventilation system 180 includes a return vent 182 and a supply vent 184. The ventilation system 180 provides air circulation to cause the air to be drawn into the return vent 182.

Based on the size of the enclosed area 190, the capacity of the ventilation system 180 may be determined. That is, the larger the dimension of the enclosed area 190 is, the bigger the capacity of the ventilation system 180 is. Further, based on the size of the enclosed area 190, the number of the supply vents 184 and the return vents 182 may also be determined. In an aspect, the dimension of the supply vent 184 into the enclosed area 190 may be smaller than the dimension of the return vent 182. In an aspect, one or more supply vents 184 and return vents 182 may be connected to the ventilation system 180.

The detection sensor 110 may be installed in the return vent 182. Since the air inside the enclosed area 190 is circulated through the return vent 182, the detection sensor 110 may sense a vaping cloud 195 and identify the vaping when there is vaping activity in the enclosed area 190. In a case when multiple return vents 182 are connected to the ventilation system 180, the detection sensor 110 may be installed in each of the return vents 182 or in the nearest vent to the supply vent 184.

Based on the speed of the air movement/airflow, the detection sensor 110 may control the sampling rate to sense the air. In accordance with aspects of the present disclosure, a faster speed of the air/airflow corresponds to a higher sampling rate of the detection sensor 110. Thus, the air quality sensor of the detection sensor 110 may increase the sampling rate of the air as the speed of the air/airflow increases and may lower the sampling rate as the speed of the air/airflow decreases.

In various embodiments, the detection sensor 110 may adjust sensitivity parameters based on the speed of the air movement/airflow. In accordance with aspects of the present disclosure, a faster speed of the air/airflow corresponds to a higher sensitivity level for vape/air quality detection by the detection sensor 110.

The air inside the enclosed area 190 may be drawn into the return vent 182 due to mechanisms of the ventilation system 180, which can include a fan. Further, the sampling rate and/or sensitivity of the air quality sensor of the detection sensor 110 may be determined based on the rate of airflow between the supply vent 184 and the return vent 182. Thus, a higher rate of airflow corresponds to a higher sampling rate and/or more sensitivity, and vice versa.

Moisture and dust particles are generally included in the vaping cloud 195 and the air in the enclosed area 190. Thus, the detection sensor 110 may be made of materials resistant to moisture and dusts. In an aspect, the detection sensor 110 may include a filter to filter out dusts and/or moisture. Further, the detection sensor 110 may send an alert if the filter is clogged and needs to be changed.

In an aspect, the detection sensor 110 may be installed at the entrance of the return vent 182. In another aspect, the detection sensor 110 may be installed along an air pathway where the air moves through the return vent 182. The installation location of the detection sensor 110 may be determined based on air dynamics around the entrance of the return vent 182 so that the detection sensor 110 may be exposed to the air more than any other place.

The sampling rate of the detection sensor 110 may be also determined based on the environment data collected during the learning mode. While the air is circulated by the ventilation system 180, the sampling rate of the air quality sensor of the detection sensor 110 may be adjusted and updated so that the air quality sensor may be capable of identifying vaping.

Now referring back to FIG. 2, a functional block diagram of the detection sensor 110 of FIG. 1 is shown in accordance with embodiments of the present disclosure. The detection sensor 110 may include an air quality sensor 210, a network interface 230, a power unit 240, and a controller 250. As shown in the dotted lines, a sound sensor 220 for detecting bullying is not necessary but may be included in the detection sensor 110. The sound sensor 220 may be used for detecting sound for bullying and the air quality sensor 210 may be used for detecting air quality.

The air quality sensor 210 may detect air quality including moisture and hydrogen content in the air and temperature of the air. In other words, the air quality sensor 210 may include a combination of sensors sensing air quality. In an aspect, the air quality sensor 210 may include other sensors sensing air content of the environment, such as air content of the air circulated through the return vent 182.

Vaping may be detected by specific range combination of humidity, hydrogen, and temperature, which is defined as signature in this disclosure. Since the signature does not depend on installation locations and times, internal parameters for identifying vaping may be predetermined. However, internal sensitivity parameters of the air quality sensor 210 need training to adjust its sensitivity based on, for example, the speed of air movements or circulation. The network interface 230 may be configured to transmit sensed results to the control server 120. In an aspect, the network interface 230 may transmit a request to send an alert, when vaping is identified, to the message server 140 and the client server 160. Further, the network interface 230 may receive a command to update internal settings or parameters from the control server 120.

In an aspect, the network interface 230 may communicate with others wirelessly or via a wired connection. Wireless connections may be wide area network (WAN), local area network (LAN), personal area network (PAN), ad hoc network, cellular network, etc. Wired network may utilize category 5 cable (CAT5), CAT5E, category 6 cable (CAT6), or similar cables. The sound sensor 220, the air quality sensor 210, and the network interface 230 may be powered by the power unit 240. Regular batteries may be installed to supply power to the detection sensor 110. For example, AA, AAA, or other suitable batteries may be used. The power unit 240 may utilize batteries and a connection to a power outlet so that the power unit 240 may supply power by using the batteries just in case when the power is out.

In an aspect, the power unit 240 may receive power supplied from a network cable, such as CAT5 or CAT6, which is called Power-over-Ethernet (PoE) or active Ethernet. PoE+ and 4PPoE may be also used to supply power. Since the network cable supplies power, the detection sensor 110 may be installed everywhere the network cable can be installed without worrying about a distance to a power outlet. Also, since the power unit 240 does not need electric components necessary for connections to a power outlet, manufacturing cost can be lowered and the size of the detection sensor 110 can be reduced. The detection sensor 110 further includes the controller 250, which controls functions and settings of the detection sensor 110. When the detection sensor 110 is powered, the controller 250 sets settings of the detection sensor 110 and internal parameters of the sound sensor 220 and the air quality sensor 210. The controller 250 further controls the network interface 230 to transmit detected results or requests for sending alerts when vaping is detected, and reset or update settings and internal parameters upon reception of update command from the control server 120.

The controller 250 may be implemented on Linux, Windows, android, IOS, or similar software operation system. In an aspect, the controller 250 may be implemented on a hardware system, such as a digital signal processor (DSP), application-specific integrated circuit (ASIC), field-programmable gate array (FPGA), different types of programmable read-only memory (e.g., PROM, EPROM, EEPROM, etc.), microprocessor, or microcontroller.

In an aspect, the controller 250 may be implemented on a hardware system by removing unnecessary features from the hardware system to reduce power consumption and integrating necessary features for identification into the hardware system. For example, the controller 250 may be implemented on a Raspberry Pi by removing unnecessary features, which were already equipped in the Raspberry Pi, and by integrating features for identifying vaping. In this way, power required for running the sound sensor 220, the air quality sensor 210, the network interface 230, and the controller 250 can be sufficiently supplied via a network cable. This approach for reducing power consumption may be applied to other hardware systems or software operating systems.

In an aspect, the detection sensor 110 may not be equipped with a warning system. Thus, when vaping is detected at the installation site, any person who vapes cannot recognize that the identification of such is reported to the clients 170 and the notification subscribers 150 because the identification is reported silently to the person.

Figure 4:
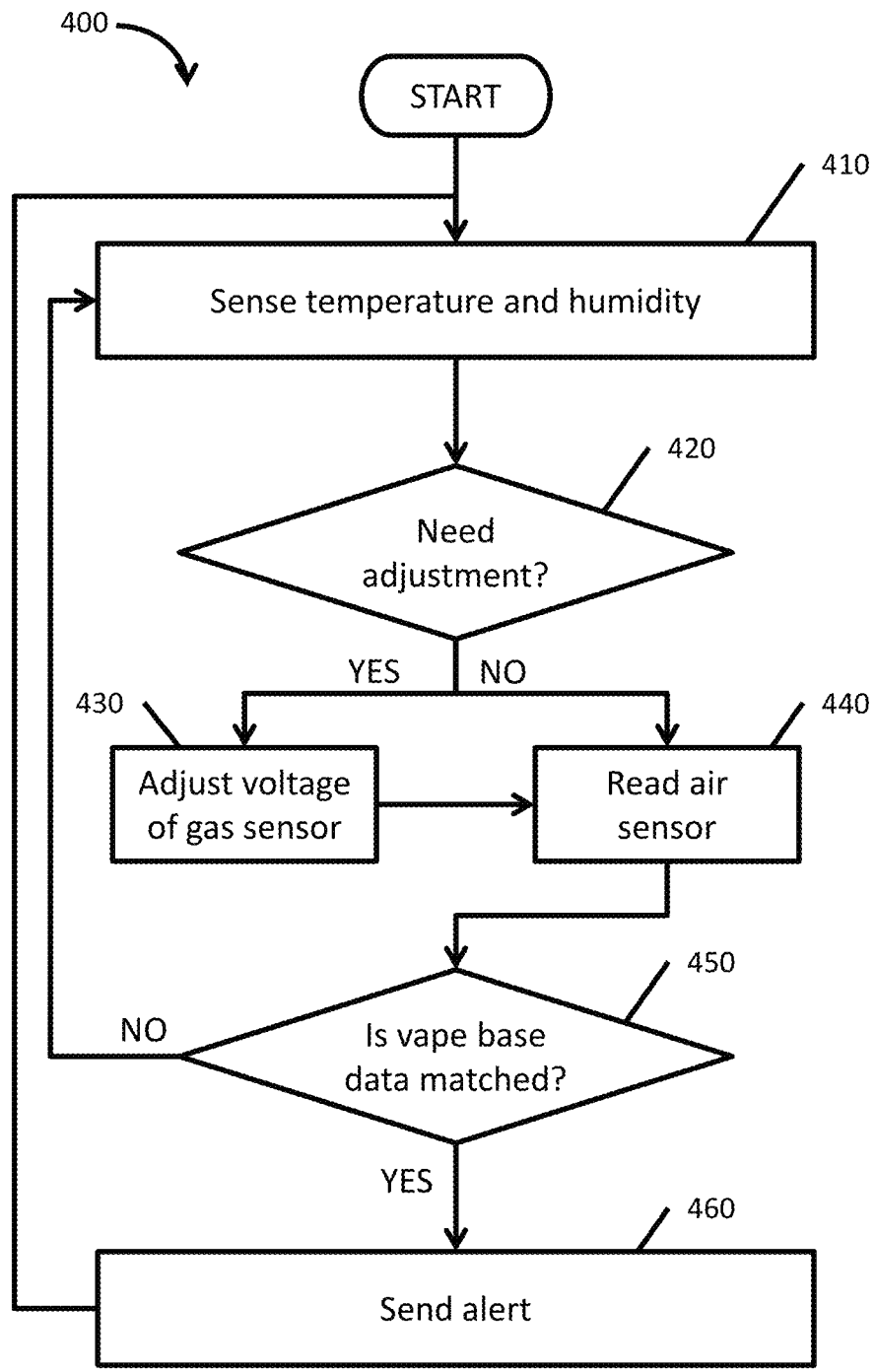
FIG. 4 is a flowchart showing an exemplary method for detecting vaping in accordance with embodiments of the present disclosure.

Turning now to FIG. 4, a flowchart is provided for a method 400 for detecting vape in accordance with embodiments of the present disclosure. The method 400 starts from sensing temperature and humidity in step 410. As described above, the modified hydrogen sensor of the detection sensor may vary because the voltage or resistance in the modified hydrogen sensor varies depending on temperature of the environment. Thus, in step 420, it is determined whether an adjustment to the modified hydrogen sensor is needed.

When it is determined that the adjustment is needed in step 420, the voltage or resistance of the modified hydrogen sensor is adjusted to appropriately sense gas (e.g., hydrogen) in step 430 and then the method 400 moves to step 440.

In an aspect, steps 410-430 may be performed during a predetermined period in a learning mode to generate base data for vaping identification. The base data may be compared with the air signature for vaping identification and used to update or adjust internal sensitivity parameters for the detection sensor.

When it is determined that the adjustment is not needed in step 420, the modified air sensor reads gas in step 440.

In step 450, it is determined whether the sensed temperature, humidity, and gas match the signature, meaning that the sensed results are within the corresponding ranges for identifying vaping. Thus, when they match the signature, an alert is sent in step 460. Otherwise, the method 400 returns to step 410 and repeats steps 410-460.

In an aspect, after the learning mode is performed, only steps 410, 440, 450, and 460 may be performed in the active mode. In case when the learning and active modes are repetitively performed, steps 410-460 may be also repetitively performed. In an aspect, based on arrangement of the active and learning modes, steps 410-460 may be arranged likewise.

Figure 5:
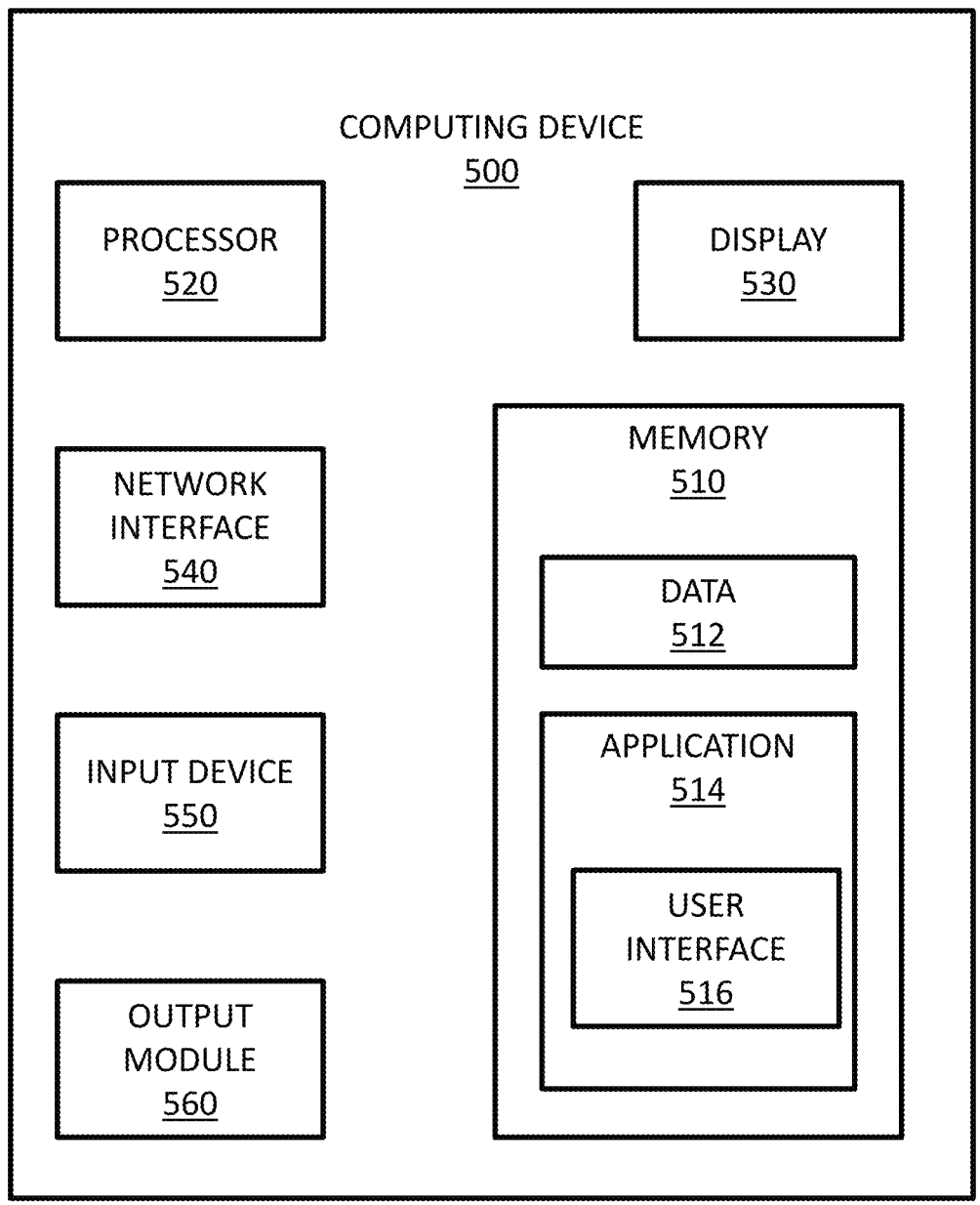
FIG. 5 is a block diagram of an exemplary computing device in accordance with embodiments of the present disclosure.

Turning now to FIG. 5, a simplified block diagram is provided for a computing device 500, which can be implemented as the control server 120, the database 130, the message server 140, and the client server 160 of FIG. 1. The computing device 500 may include a memory 510, a processor 520, a display 530, a network interface 540, an input device 550, and/or an output module 560. The memory 510 includes any non-transitory computer-readable storage media for storing data and/or software that is executable by the processor 520 and which controls the operation of the computing device 500.

In an aspect, the memory 510 may include one or more solid-state storage devices such as flash memory chips. Alternatively or in addition to the one or more solid-state storage devices, the memory 510 may include one or more mass storage devices connected to the processor 520 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 520. That is, computer readable storage media may include non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 500.

Figure 2:
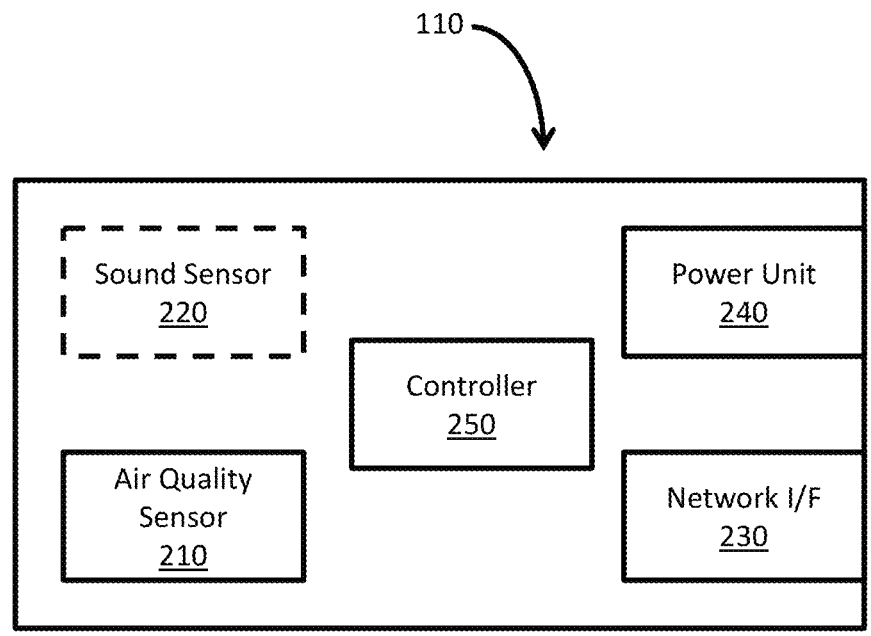
FIG. 2 is a block diagram of an exemplary sensor in accordance with embodiments of the present disclosure.

The memory 510 may store application 514 and/or data 512 (e.g., base data and history data from the sound sensor 220 and the air quality sensor 210 of FIG. 2). The application 514 may, when executed by processor 520, cause the display 530 to present the user interface 516 including FIG. 3. The processor 520 may be a general-purpose processor, a specialized graphics processing unit (GPU) configured to perform specific graphics processing tasks while freeing up the general-purpose processor to perform other tasks, and/or any number or combination of such processors. The display 530 may be touch-sensitive and/or voice-activated, enabling the display 530 to serve as both an input and output device. Alternatively, a keyboard (not shown), mouse (not shown), or other data input devices may be employed. The network interface 540 may be configured to connect to a network such as a local area network (LAN) consisting of a wired network and/or a wireless network, a wide area network (WAN), a wireless mobile network, a Bluetooth network, and/or the internet.

In an aspect, the computing device 500 may receive, through the network interface 540, detection results for the detection sensor 110 of FIG. 1, for example, history data, which is time-series data including detected air quality from the detection sensor 110 for the whole running times or a predetermined period. The computing device 500 may receive updates to its software, for example, the application 514, via the network interface 540. The computing device 500 may also display notifications on the display 530 that a software update is available.

The input device 550 may be any device by means of which a user may interact with the computing device 500, such as, for example, a mouse, keyboard, foot pedal, touch screen, and/or voice interface. The output module 560 may include any connectivity port or bus, such as, for example, parallel ports, serial ports, universal serial bus (USB), or any other similar connectivity port known to those skilled in the art. The application 514 may be one or more software programs stored in the memory 510 and executed by the processor 520 of the computing device 500. The application 514 may be installed directly on the computing device 500 or via the network interface 540. The application 514 may run natively on the computing device 500, as a web-based application, or any other format known to those skilled in the art.

In an aspect, the application 514 will be a single software program having all of the features and functionality described in the present disclosure. In other aspect, the application 514 may be two or more distinct software programs providing various parts of these features and functionality. Various software programs forming part of the application 514 may be enabled to communicate with each other and/or import and export various settings and parameters relating to the identification of vaping. The application 514 communicates with a user interface 516 which generates a user interface for presenting visual interactive features to the notification subscribers 150 or the clients 170 of FIG. 1 on the display 530. For example, the user interface 516 may generate a graphical user interface (GUI) and output the GUI to the display 530 to present graphical illustrations such as FIG. 3.

Since other modifications and changes may be made to fit particular operating requirements and environments, it is to be understood by one skilled in the art that the present disclosure is not limited to the examples described in the present disclosure and may cover various other changes and modifications which do not depart from the spirit or scope of this disclosure.

What is claimed is:

1. A sensor system for identifying vaping and smoking at an enclosed area, wherein air within the enclosed area is supplied via a supply vent and returns to the return vent, the sensor system comprising:
   an air sensor located at or adjacent to an entrance of a return vent of a ventilation system, which circulates the air within the enclosed area, and configured to sense air quality of the air circulated to the return vent;
   a controller configured to identify the vaping and smoking from the sensed air quality based on an air signature stored in a database in communication with the controller; and
   a network interface configured to communicate an alert indicating the vaping or smoking, when the vaping or smoking is identified,
   wherein the controller is further configured to adjust internal sensitivity parameters of the air sensor for identifying the vaping and smoking at the enclosed area based on a rate of airflow between the return and supply vents of the ventilation system.

2. The sensor system according to claim 1, further comprising a power connection implementing at least one of: Power over Ethernet, Power over Ethernet+, or power by a power outlet.

3. The sensor system according to claim 1, wherein the air sensor is configured to sample the air conveyed through the return vent at a sampling rate based on airflow of the air conveyed through the return vent.

4. The sensor system according to claim 3, wherein the sampling rate for a higher airflow is greater than the sampling rate for a lower airflow.

5. The sensor system according to claim 1, wherein the internal sensitivity parameters are adjusted to be more sensitive for a higher airflow of the air than for a lower airflow of the air.

6. The sensor system according to claim 1, wherein the air sensor is trained by data collected at the enclosed area during a predetermined period in a learning mode prior to identification of the vaping or smoking.

7. The sensor system according to claim 6,
   wherein the controller is further configured to adjust the internal sensitivity parameters based on the collected data during the predetermined period in the learning mode.

8. The sensor system according to claim 7, wherein the controller is configured to adjust the internal sensitivity parameters by comparing the collected data with the air signature.

9. The sensor system according to claim 7, wherein the air signature includes a temperature range, a hydrogen range, a humidity range, a particulate concentration range, and a particulate mass range.

10. The sensor system according to claim 1, wherein the alert includes at least one of a text message, an email, an optical flashing, or an audible sound.

11. A detection system for identifying vaping and smoking at an enclosed area, wherein air within the enclosed area is supplied by the supply vent and returns to the return vent, the detection system comprising:
   a ventilation system including a return vent and a supply vent and circulating the air within the enclosed area; and
   a sensor system located at or adjacent to an entrance of the return vent, the sensor system comprising:
   an air sensor configured to sense air quality of the air circulated to the return vent,
   a controller configured to identify the vaping and smoking from the sensed air quality based on an air signature stored in a database in communication with the controller, and
   a network interface configured to communicate an alert indicating the vaping or smoking, when the vaping or smoking is identified, wherein the controller is further configured to adjust internal sensitivity parameters of the air sensor for identifying the vaping and smoking at the enclosed area based on a rate of airflow between the return and supply vents of the ventilation system.

12. The detection system according to claim 11, wherein the sensor system further includes a power connection implementing at least one of: Power over Ethernet, Power over Ethernet+, or power by a power outlet.

13. The detection system according to claim 11, wherein the air sensor is configured to sample the air conveyed through the return vent at a sampling rate based on airflow of the air conveyed through the return vent.

14. The detection system of claim 13, wherein the sampling rate for a higher airflow is greater than the sampling rate for a lower airflow.

15. The detection system according to claim 11, wherein the internal sensitivity parameters are adjusted to be more sensitive for a higher airflow of the air than for a lower airflow of the air.

16. The detection system according to claim 11, wherein the air sensor is trained by data collected at the enclosed area during a predetermined period in a learning mode prior to identification of the vaping or smoking.

17. The detection system according to claim 16, wherein the controller is further configured to adjust the internal sensitivity parameters based on the collected data during the predetermined period in the learning mode.

18. The detection system according to claim 17, wherein the controller is further configured to adjust the internal sensitivity parameters by comparing the collected data with the air signature.

19. The detection system according to claim 18, wherein the air signature includes a temperature range, a hydrogen range, a humidity range, a particulate concentration range, and a particulate mass range.

20. The detection system according to claim 11, wherein the alert includes at least one of: a text message, an email, an optical flashing, or an audible sound.

21. A method for identifying vaping and smoking at an enclosed area, wherein air within the enclosed area is supplied via a supply vent of the ventilation system and returns to the return vent, the method comprising:
  collecting data by an air sensor located at or adjacent to an entrance of a return vent of a ventilation system, which circulates the air within the enclosed area, and configured to sense air quality of the air circulated to the return vent during a predetermined period in a learning mode;
  adjusting, by a controller in communication with the air sensor, based on the collected data, internal sensitivity parameters of the air sensor for identifying the vaping or smoking;
  sensing air quality by the air sensor of air conveyed through the return vent;
  identifying, by the controller, the vaping or smoking from the sensed air quality based on an air signature stored in a database in communication with the controller; and
  communicating via a network interface in communication with the controller an alert when the vaping or smoking is identified,
  wherein the internal sensitivity parameters of the air sensor are further adjusted by the controller for identifying the vaping and smoking at the enclosed area based on a rate of airflow between the return and supply vents of the ventilation system.

22. The method according to claim 21, wherein the air signature includes a temperature range, a hydrogen range, a humidity range, a particulate concentration range, and a particulate mass range.

23. The method according to claim 21, wherein adjusting the internal sensitivity parameters includes adjusting the internal sensitivity parameters of the air sensor by comparing the collected data with the air signature.

* * * * *